United States Patent [19]

D'Aoust

[11] Patent Number: 4,563,892

[45] Date of Patent: Jan. 14, 1986

[54] TOTAL DISSOLVED GAS PRESSURE MEASURING DEVICE

[76] Inventor: Brian G. D'Aoust, 7595 Finch Rd. NE., Bainbridge Island, Wash. 98110

[21] Appl. No.: 634,147

[22] Filed: Jul. 24, 1984

[51] Int. Cl.$^4$ ............................................. G01N 7/10
[52] U.S. Cl. ...................................................... 73/19
[58] Field of Search ................... 73/19, 4 R, 747, 746, 73/749, 750, 756, 705; 55/270, 158

[56] References Cited

U.S. PATENT DOCUMENTS

| | | | |
|---|---|---|---|
| 3,313,157 | 4/1967 | Gilson | 73/747 |
| 3,459,032 | 8/1969 | Yamaguchi et al. | 73/4 R |
| 4,366,700 | 1/1983 | Bouck | 73/19 |

FOREIGN PATENT DOCUMENTS

684865 12/1952 United Kingdom ..................... 73/19

*Primary Examiner*—Stephen A. Kreitman
*Attorney, Agent, or Firm*—Cole, Jensen & Puntigam

[57] ABSTRACT

The invention measures the total dissolved gas and fluid vapor pressure in liquids both aqueous and organic. It comprises a hydrostatically isolated gas phase of as low volume as possible isolated from the liquid being measured by a gas-permeable membrane configured to be insensitive to hydrostatic pressure, in this instance in the form of a tube. The gas phase inside the tube communicates with a pressure measuring component which is either, in this instance, a special type of closed manometer, or strain gauge which senses pressure by piezoresistive or capacitive pressure induced change or other pressure measuring means of low or negligible internal volume and compliance, together with a calibration means. The invention is provided with a calibrated scale or electronic readout means for the pressure measuring component.

17 Claims, 2 Drawing Figures

TOTAL DISSOLVED GAS PRESSURE MEASURING DEVICE

BACKGROUND OF THE INVENTION

The invention relates to instruments and techniques for measuring the total amount of gas dissolved in a liquid, solvent or solution and more particularly to a new and improved apparatus for measuring total dissolved gas pressure in fluids.

The determination of total, as contrasted to individual or partial, gas pressures provides valuable information as to the degree to which equilibrium with the gaseous environment or the atmosphere has been established. For the purposes of this discussion and description, total dissolved gas pressure in a liquid means the sum total of all partial pressures of all gases dissolved in the liquid including the vapor pressure of the liquid. Total gas pressure information is also valuable in studies to determine relationships between excess pressures and environmental conditions which have created supersaturation problems. As mentioned above, fish and aquatic life in rivers, lakes, hatcheries, aquaria and other aquaculture projects have often died of gas embolism because of the excess total pressure of dissolved gases in these various bodies of water. Such a condition facilitates bubble formation in the organisms with fatal results. As a result, instruments capable of quickly and easily providing the dissolved gas pressure information are currently used and increasingly needed both to study the condition of "gas bubble disease" and to monitor waters where there is any likelihood of danger or risk to fish and aquatic life.

As those skilled in the art are aware, water in which there is as little as 10% or perhaps even less excess of dissolved gas can be lethal to fish life. Any pumped or otherwise pressurized water supply can present a risk and hence it is necessary to know the levels of air or dissolved gases in a particular system. In addition, many industries aerate or sparge water or other fluids with air or other gases to saturate with or remove air or other gases. Measuring techniques such as that herein described facilitate economical quality control where used.

Instruments and techniques for measuring total dissolved gas and fluid vapor pressures in solutions have for the most part been concerned with particular gaseous components as opposed to measuring the total pressure of all gases dissolved in the fluid. Some of the more obvious applications of a device for measuring total dissolved gases are in the area of water pollution, industrial and other waste water analysis, fish hatchery water quality, aquarium water quality, wine, beer and beverage production and any other application where it is desired to assess the state of gas pressure equilibrium or disequilibrium between the water or fluid and a gas phase. Accordingly, the invention's recent application to water quality and atmospheric saturation is an obvious example of general applications requiring knowledge of the saturation state of any liquid with any gas phase, although an external gas phase per se is not necessary for the measurement. Clearly, these more general uses include numerous industrial and even space applications, and provide a new analytical method of greater convenience and simplicity.

Current state-of-the-art instrumentation is unnecessarily cumbersome and expensive. Some of the prior instruments, sometimes referred to as "saturometers" or "gasometers", require time consuming and tedious procedures, sometimes require water pumps and as a result present prohibitive disadvantages if a large number of measurements must be taken to monitor a relatively large body of water, or if remote measurements at depth must be made. Additionally, known "saturometers" and "gasometers" and their use require skill and training in the operators, are very susceptible to damage and do not provide an absolute pressure reading but a gauge pressure which due to barometric pressure fluctuations is subject to error. Also, the use of dial gauges employing a Bourdon tube imposes further equilibration time requirements and gradual gauge errors due to corrosion; further the use of mercury in an open-ended manometer increases the size of the devices using it. Additionally, such devices all require an operator or observer at the measuring site which increases the cost of measurements and decreases the utility of the devices. The above are among the more apparent disadvantages of present equipment and devices.

Among the known prior art publications relating to this subject matter are the following United States Letters Patent.

U.S. Pat. No. 3,438,241 is a structurally unrelated device which is directed toward selected gas pressure measurement as opposed to total dissolved gas pressure.

U.S. Pat. No. 3,871,228 is directed to a device for total pressure measurement but structurally and functionally is significantly different from that of the instant application.

U.S. Pat. No. 4,366,700 also measures total dissolved gas dissolved in a fluid but again is also structurally significantly different from the instant device.

U.S. Pat. Nos. 3,668,837 and 3,673,864 are of interest only and significantly unrelated to the specifics of the instant invention.

SUMMARY OF THE INVENTION

The invention utilizes a gas-permeable membrane which in the instant device is most conveniently provided in the form of tubing both to separate the fluid phase from the gas phase and to connect the gas phase behind the membrane to one arm of a specially configured manometer. The other arm of the manometer communicates with an accurately known gas volume. Other types of pressure sensing systems behind the membrane can be used provided they are of low internal volume and compliance. The gas phase volume behind the membrane and between the gas phase side of the membrane and the pressure responsive and sensing medium is designed to be held to a minimum and thus the total internal geometric gas phase volume of the device is also held to a minimum. The device has adjustment or calibration features which enable the unique manometer to be accurately calibrated by the use of a length vs. pressure scale, and an equalizing and zeroing valve as well as a manometer liquid reference volume adjustment incorporated into construction of the manometer.

Accordingly, it is among the many features and advantages of the invention to provide a total gas pressure monitor which is compact, small and position-insensitive, and which can be configured to make its use convenient to the user and which can be used at the site of the liquid to be measured or the body of water to be monitored. The unit in simplest form, is non-electronic, it is simpler than known devices and easily maintained. As mentioned above, it includes adjustment or zeroing features and easily replaceable membranes not taught in the prior art and of particular importance in many industrial applications can include an electrical switch for relay operation at a preset pressure level. In the special manometer configuration, only one arm of the manometer need be visible next to the calibrated scale.

The readout scale is non-linear but nevertheless precise and accurate in its measurement. Further, it is possible to accurately change the volume of the reference side of the manometer so as to accommodate several different pressure ranges in one device, a convenience not available in any of the prior art. The device holds the internal gas phase volume to a minimum so that the time for obtaining a measurement is greatly reduced, as is also reduced the possibility of errors from bubble formation on the surfaces of the membrane.

DESCRIPTION OF PREFERRED EMBODIMENTS

Figures 1, 2:
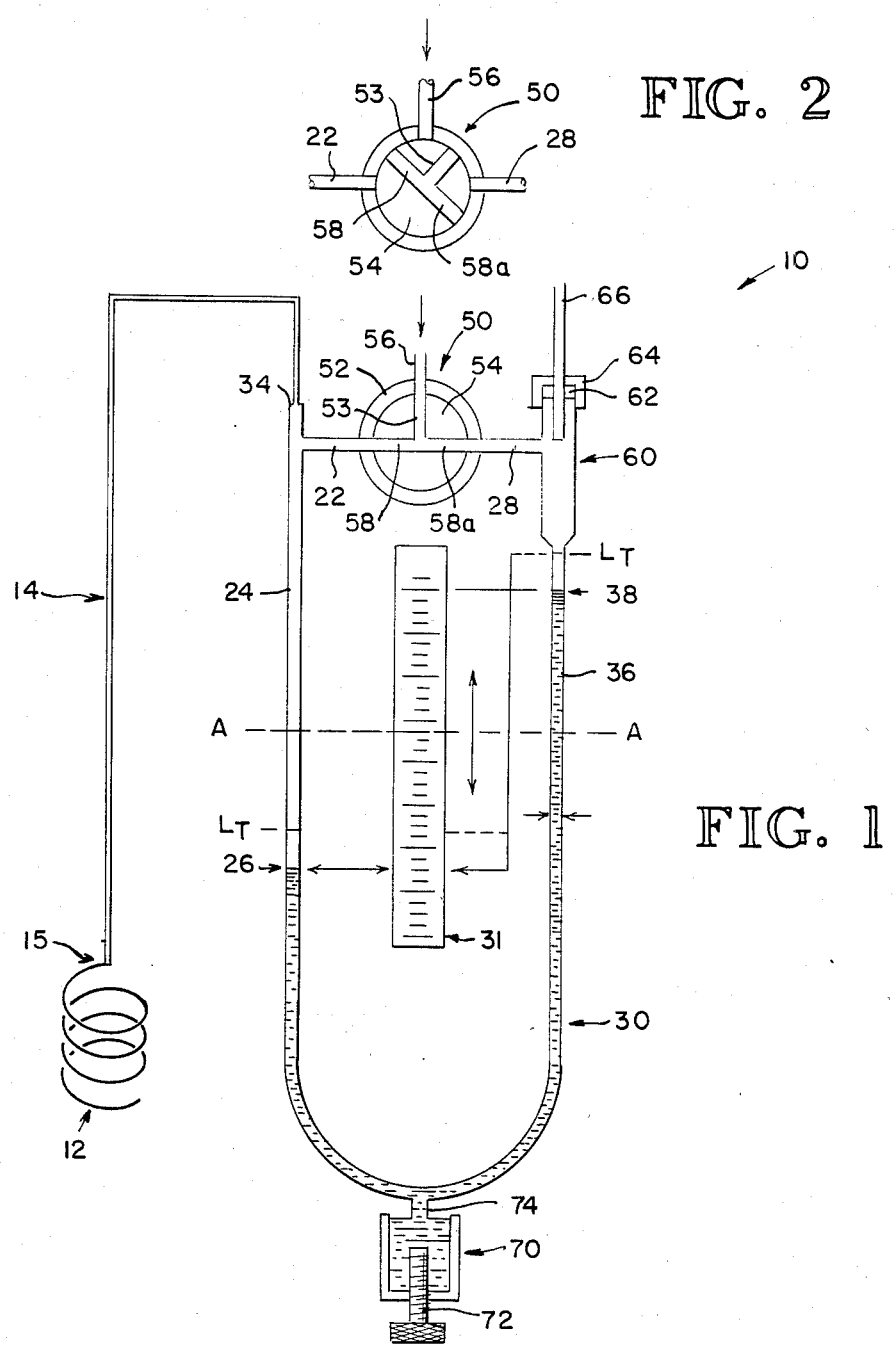
FIG. 1 of the drawings shows the essential features and arrangement of the parts of the measuring device of this invention utilizing the closed manometer configuration.
FIG. 2 shows the zeroing valve closed after the manometer has been calibrated.

Referring now to the drawings, it will be seen that the measuring device, generally designated by the number 10, includes a number of parts or components which are combined in a unique and novel way to comprise the invention.

As those skilled in the art are aware, each liquid has a unique capacity for each gas and this capacity is different at every temperature. When more gas is dissolved in a liquid than can be in equilibrium with the atmosphere or gas-phase above the liquid or the gas phase with which the liquid is in contact, referred to as the liquid's "solubility" for that gas at the total pressure and temperature of the system, it is said that a state of supersaturation exists. On the other hand, if less gas is dissolved than the liquid could "hold" at a given pressure or temperature, i.e. than is consistent with its solubility or capacity for that gas at the prevailing temperature and pressure, it is said that the liquid is undersaturated. Since, to the extent relevant to this device, each gas is independent and unaffected by any other gas in a mixture of gases in contact with a fluid, each gas has a partial pressure which directly determines its resulting concentration at equilibrium in the liquid. Since the total dissolved gas pressure is the sum of all gas or vapor partial pressures, a direct measurement of total dissolved gas pressure indicates the state of gas saturation of the liquid. In other words, the invention measures whether the liquid is under- or over-saturated with respect to the pressure of the atmosphere or gas phase with which it is in contact.

The invention shown in FIG. 1 utilizes a gas-permeable tubular membrane, generally designated by the number 12, to separate the liquid phase which is being tested or monitored, from a gas phase of minimal volume behind the gas-permeable membrane. Membrane 12 is shown as a very fine tube, preferably a medical grade silicone tubing which by way of example only may have an outside diameter of 0.025 inches and an inside diameter of 0.012 inches. The time required for diffusion of the gases through the membrane depends on the ratio of the membrane's surface area, to the internal volume of the device. In the instant invention, the length of the membrane tubing probe, its internal volume, and the remaining internal volume connecting the tubing probe to the pressure sensing surface, determines that surface area to internal volume relationship.

Connected to the permeable tubing membrane 12 at point 15 is a gas-impermeable tubing 14 which connects at point 34 to the left leg 24 of manometer 30. Tubing 14 is connected to the manometer leg 24 at point 34. The surface of the manometer pressure sensing fluid level is indicated at point 26, with the slightly elevated and shaded portion also above point 34 exaggerated in order to represent thermal expansion of the fluid. It will be understood that the manometer 30 is of small bore using a manometric fluid of negligible vapor pressure such as silicone oil in contrast to a necessarily longer open-armed mercury manometer. It will be noted that short sections 22 and 28 of the manometer arms lead to valve 50 which will be described more fully hereinafter. The impermeable tubing 14 and manometer leg 24 allow the gas pressure to be transmitted from probe 12 to the manometer fluid so that at equilibrium the difference between the dissolved gas pressure and the pressure in the right hand chamber 60 will be shown by the difference in height of the fluid in the right side or leg 36 of the manometer above the zero point A. This difference is read with reference to a calibrated scale. It will be understood that the valve 50 described below is used to equalize the pressure on either side of the manometer prior to measurement.

At the end of leg 36 of manometer 30 is a reference volume chamber 60 having a seal 62, closure member or cap 64 and volume adjustment screw 66 or other adjustment means which extends through the gas-tight closure 64 into the chamber 60. A passage 28 interconnects chamber 60 with valve 50 just as passage 22 on the other side connects leg 24 of the manometer with valve 50.

The valve has a housing 52 with an inlet line 56 for external atmospheric or reference air pressure. A valve portion 54 of valve 50 includes connector passages 53, 58 and 58a which interconnect with passages 22, 28 and 56 for initial zeroing of the device which will be more fully explained hereinafter. Although the configuration of value 50 is shown schematically as a laboratory stopcock, any valve configuration incorporating minimal gas volume fulfilling these functions will suffice. It will be appreciated from the above that the measuring device 10, unlike a typical mercury manometer, is closed on the reference side thus making the invention a more compact but non-linear measuring device for registering the pressure on scale 31. It will also be understood that by trapping a reference volume in chamber 60, orientation during measurement also becomes unimportant in contrast to the mercury manometer of the prior art. Hence, the attitude or angular positioning of the device need not be considered when it is being used provided that the bore or internal diameter of the manometer is not too large. This is of considerable advantage in comparison to prior art equipment because it allows more versatility in obtaining measurements in many different circumstances.

In use, and before making a measurement, the unit 10 is zeroed by having valve 50 in the position shown in FIG. 1, thus allowing both arms of the manometric fluid to reach the level along dotted line A—A. A reservoir 70 is provided at the bottom of the manometer loop with an interconnecting passage 74 to the manometer tubing and an adjustment screw or other adjustment means 72 for adjusting the manometer fluid level so that the surfaces 26 and 38 are on line A—A. Once the zero reference has been accomplished, the valve 50 is turned to its off position as shown in FIG. 2 thus isolating the two sides of the manometer and leaving atmospheric pressure in chamber 60. Again, the exact volume of chamber 60 can be adjusted with the adjustment screw or rod 66 prior to the zeroing manipulation, and depending upon the preselected pressure range desired.

The reference volume of chamber 60 is adjusted so that for each increment of total dissolved gas pressure increase or decrease exerted on the left-hand side of the manometer, a decrease or increase in the volume of chamber 60 will be realized according to the relationship $P \times V = n \times R \times T$, where P is pressure in atmospheres, V is the volume in liters, n is moles or gram molecular weight of the gas, R is the gas constant of the equation of state of the gas (liter-atmospheres per mole per degree), and T is the absolute or Kelvin temperature. This general form of the gas law allows the calculation of the length of the liquid column on the right hand side of the manometer at constant pressure and temperature, assuming its bore is precisely linear, a requirement well within present technology. Since the volume change related to a given pressure change can be calculated from the equation, it follows that if the bore of arm 36 of the manometer 30 is constant, the length of the fluid excursion due to a given pressure change can similarly be calculated. In other words, if the chamber volume of chamber 60 is known then each additional increment of pressure will have a predictable incremental affect on the fluid column length in the right-hand arm 36 of the manometer. In this way, the scale 31 can be pre-established for any known volume of chamber 60 to give a clear accurate reading of the total dissolved gas pressure measured. Further, this scale reading can be pre-calculated in "% saturation" if desired, since it is always relative to the initial atmospheric pressure prior to measurement and closing of valve 52.

From the above, it will be understood that the volume of chamber 60 and the diameter or bore of the right sides or arms 36 of the manometer are chosen and/or adjusted to suit the expected pressure range. The scale 31 is designed and delineated to accommodate the inherent fractional decrease in the length of the right hand fluid column with increased pressure applied to the left hand side or arm 24 of the manometer.

Alternatively, the bore of arm 36 can be tapered to just the right degree to automatically compensate for the non-linearity thus allowing use of a linear scale. Once calibrated, that is, once the relationship of pressure and length of fluid on the right hand side 36 of the manometer is known, the device is subject to relatively few errors except temperature, and this error is eliminated if the reference volume 60 is immersed in the measured liquid or thermostated at constant temperature by some other means. It can be operated in any position independently of gravity which is not possible with conventional mercury manometers or some Bourdon type tube gauges. Thus the device lends itself to total immersion.

Alternative configurations of the device involve a flat membrane supported by porous material which serves the dual function of mechanical protection of the gas phase from hydrostatic or mechanical pressure and membrane support. In this configuration, the device lends itself to current piezoresistive and capacitance-sensitive integrated circuit pressure sensors which can be fabricated with very low internal volume.

Another advantage of the device is its suitability for remote industrial control purposes to act as an on-off switch, relay or remote indicating device by using the manometer fluid as an electrical conductor, capacitance or light path so as to be able to remotely monitor the existence or non-existence of a pre-set pressure. This remote position readout can be accomplished directly in several ways, including using the fluid as part of an electrical circuit either directly as a current path or indirectly as a capacitance change, conductive or magnetic change, or optically sensed light path. The magnetically sensed change for example would be accomplished by using a magnetic fluid as the manometer fluid, and a simple magnetic sensor such as a Hall unit or magnet diode. The optical means can be used to provide a measure of the length of fluid arm 36 of the manometer, thereby converting the device to one providing analog electrical output, while maintaining the advantages noted above.

What is claimed is:

1. A total dissolved gas pressure measuring device for liquids, comprising:
   (a) a minimal internal volume partly bounded by a gas permeable membrane formed so as to separate the liquid from said minimal internal volume,
   (b) a connecting volume on the gas phase side of said membrane between said membrane and a pressure responsive means such that the volume thereof is as small as possible and resistant to hydrostatic pressure so that for changes in measured total gas pressure the changes in gas content of the internal volume space are also as small as possible,
   (c) means for maintaining constancy of said internal volume on said gas phase side of said membrane, and
   (d) a gas pressure measuring means connected to and partly bounding said internal volume space so as to define a closed connection, said gas pressure measuring means including a pressure sensitive surface to be contacted by said gas and said pressure measuring means also including a pressure responsive, visual read-out means for registering pressure exerted by said gas on said pressure sensitive surface.

2. The gas pressure measuring device according to claim 1 and in which said gas permeable membrane is in the form of flexible tubing and said internal volume space is at least partially formed of gas-impermeable tubing.

3. The gas pressure measuring device according to claim 2 and wherein said pressure measuring means is a closed and non-linear, adjustable manometer with one leg connected to said impermeable tubing.

4. The gas pressure measuring device according to claim 3 and wherein the manometric fluid of said manometer is electrically conductive.

5. The gas pressure measuring device according to claim 3 and wherein the manometric fluid of said manometer is a dielectric material.

6. The gas pressure measuring device according to claim 3 and wherein the manometric fluid of said manometer is ferromagnetic.

7. The gas pressure measuring device according to claim 3 and wherein the manometric fluid of said manometer is an optical dye material.

8. The gas pressure measuring device according to claim 3 and wherein said manometer has a pressure adjustment valve means connected to both legs thereof such that the pressure on said both legs is equalized before use of the device in its closed measuring mode.

9. The gas pressure measuring device according to claim 8 and in which said manometer also has internal volume calibration means connected to the other leg so that the volume of air or gas closed within said manometer other leg can be predetermined for non-linear movement of said manometric fluid.

10. The gas pressure measuring device according to claim 9 and in which said manometer further includes manometric liquid adjustment means generally at the bottom thereof for adjusting the liquid levels in said legs.

11. The gas pressure measuring device according to claim 10 and in which a scale with indicia is provided with respect to said other leg of said manometer so that the non-linear movement and measurement of the manometric fluid in response to gas pressure may be visually observed and quantified.

12. A total dissolved gas pressure measuring device for liquids, comprising:
   (a) a gas-permeable membrane for separating said fluid phase from a gas phase and being formed as a flexible, tubing of predetermined inner and outer diameter and length,
   (b) a gas-impermeable tubing attached to said gas-permeable membrane and defining a part of the internal volume space such that the volume thereof is optimally small and so that for changes in measured total gas pressure the changes in gas content of this part of the internal volume space are also small,
   (c) a gas pressure measuring means connected to said gas impermeable tubing by a tubular connecting portion, said tubular connecting portion also being of minimal internal volume space so as to minimize the total internal volume space within said device, thereby minimizing the amount of gas which must diffuse into the device to obtain a reading,
   (d) said gas pressure measuring means including a closed, pressure measuring structure having a pressure sensitive surface to be contacted by said gas, said pressure measuring means also including a non-linear pressure responsive, visual read-out which is a pre-calibrated scale for said resulting non-linear pressure response.

13. The gas pressure measuring device according to claim 12 and wherein said gas pressure measuring means is a nonmercury, closed and non-linear, adjustable manometer with one leg connected to said impermeable tubing.

14. The gas pressure measuring device according to claim 13 and wherein said manometer has a pressure adjustment valve means connected to both legs thereof such that the pressure on said both legs is equalized before use of the device in its closed mode.

15. The gas pressure measuring device according to claim 14 and in which said manometer also has internal volume calibration means connected to the other leg so that the volume of air or gas closed within said manometer other leg can be predetermined for non-linear movement of said manometric fluid.

16. The gas pressure measuring device according to claim 15 and in which said manometer further includes manometric liquid adjustment means generally at the bottom thereof for adjusting the liquid levels in said legs.

17. The gas pressure measuring device according to claim 16 and in which a scale with indicia is provided with respect to said other leg of said manometer so that the non-linear movement and measurement of the manometric fluid in response to gas pressure may be visually observed.

* * * * *